United States Patent [19]

Brewster

[11] Patent Number: 4,885,150
[45] Date of Patent: Dec. 5, 1989

[54] STABLE THIOCYANOGEN COMPOSITION

[75] Inventor: Steven L. Brewster, Lake Jackson, Tex.

[73] Assignee: The Dow Chemical Company, Midland, Mich.

[21] Appl. No.: 256,895

[22] Filed: Oct. 13, 1988

Related U.S. Application Data

[63] Continuation-in-part of Ser. No. 13,487, Feb. 11, 1987, abandoned, which is a continuation-in-part of Ser. No. 834,983, Feb. 28, 1986, abandoned.

[51] Int. Cl.$^4$ .................... C09K 15/16; C09K 15/26; C09K 15/22; C01B 21/093
[52] U.S. Cl. .................................. 423/366; 252/401; 252/402; 252/403
[58] Field of Search ................ 423/366; 252/401, 402, 252/403

[56] References Cited

U.S. PATENT DOCUMENTS 3,011,976 12/1961 Cyba et al. .................. 252/401

Primary Examiner—Mary C. Lee
Assistant Examiner—Robert C. Whittenbaugh
Attorney, Agent, or Firm—A. C. Ancona

[57] ABSTRACT

The present invention is a composition comprising (a) thiocyanogen or a thiocyanogen halide and (b) an α,β-unsaturated ketone, e.g. chloranil, in solution in (c) an inert organic solvent. The composition is useful for the introduction of thiocyanate functionality into organic compounds in the same manner as thiocyanogen or thiocyanogen chloride, but is stable over longer periods of time, i.e. one year or more.

30 Claims, No Drawings

STABLE THIOCYANOGEN COMPOSITION

CROSS-REFERENCE TO RELATED APPLICATION

This is a continuation-in-part of application Ser. No. 013,487, filed Feb. 11, 1987 now abandoned which is a continuation-in-part of application Ser. No. 834,983, filed Feb. 28, 1986 which is now abandoned.

BACKGROUND OF THE INVENTION

It is known that thiocyanogen is an active compound useful for treating the surfaces of polymers to enhance the adhesion of paint applied thereto. Thiocyanogen is also useful in reacting with organic compounds to prepare organic thiocyanates or isothiocyanates.

The reaction with the polymers or with organic compounds is advantageously conducted in solution since the thiocyanogen is not normally isolable as such. Even in solution, however, the thiocyanogen is not stable and will precipitate from solution as a polymeric material which is unreactive for the purposes desired. Thus, these solutions must be used within a short period of time after preparation. Therefore, it would be highly desirable to develop a stable form of such solutions to enable them to be shipped and to be used at a time somewhat later than the time at which they are prepared.

Thiocyanogen is prepared by methods known to the art. Metal thiocyanates are oxidized, e.g. reacted with $Cl_2$, to form the thiocyanogen, $(SCN)_2$. Illustrative of this reaction is the use of potassium thiocyanates:

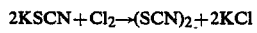

$$2KSCN + Cl_2 \rightarrow (SCN)_2 + 2KCl$$

The thiocyanates of metals of Groups IA, IIA, and IVA of the periodic chart are also useful. Examples are the thiocyanates of sodium, lithium, potassium, calcium and lead.

Oxidizing agents which can be used in place of chlorine are bromine, fluorine and organic peroxides.

A thiocyanating composition has now been discovered which has the desirable properties of the unstable thiocyanogen, but in which the tendency to polymerize is inhibited, allowing it to remain active over long periods of time.

SUMMARY OF THE INVENTION

The present invention is a stable thiocyanating composition containing (a) thiocyanogen or a thiocyanogen halide together with (b) an $\alpha,\beta$-unsaturated ketone, e.g. o-chloranil, in (c) an inert organic solvent.

This composition is less likely to form polythiocyanogen than thiocyanogen solutions previously known, remaining active for the introduction of thiocyanate functionality into organic compounds over greatly extended periods of time.

DETAILED DESCRIPTION OF THE INVENTION

The composition of the invention can be prepared by adding to a solution of thiocyanogen or a thiocyanogen halide in an inert solvent certain conjugated unsaturated ketones, i.e. the unsaturation is between the carbon atoms $\alpha$- and $\beta$- to the carbonyl group. The composition can be used in the same manner as known thiocyanogen or thiocyanogen halide solutions, but will not polymerize over an extended period of time. Thus, the product can be packaged and shipped whereas the known thiocyanogen solutions are unstable and must be used within a relatively short period of time before they polymerize and form a brick-red precipitate, thereby becoming inactive.

The composition can be used to treat the surfaces of polymers to provide a more adherent surface for paint. Thus, polyurethane manufactured products can be treated by immersing them in a solution containing the composition. The reaction which takes place provides a surface to which paint will adhere more readily. It is especially useful to treat the surface of molded polymer products in which an internal mold release, such as zinc stearate and/or silicones, has been employed, which make the surfaces of molded items especially difficult to paint. Other polymers which can be reacted with the stable thiocyanogen product of this invention to provide a more adherent surface are polypropylene, polyethylene, polystyrene, polycarbonate, polyamide, polyimide, polyester and epoxy resins.

The process of thiocyanation using the compositions of this invention can be conducted in any manner that is known for using thiocyanogen or thiocyanogen chloride solutions to react with polymers, either those containing unsaturation or with those which are fully saturated, respectively. Teachings concerning the treatment of surfaces with thiocyanogen are disclosed in U.S. Pat. No. 4,567,241 while those using thiocyanogen chloride are disclosed in U.S. Pat. No. 4,613,653. The teachings in both patents respecting such treatments are incorporated herein by reference.

The stable compositions of the invention can also be used to react with other simpler organic compounds to prepare thiocyanate derivatives. Thus, unsaturated aliphatics such as cyclohexene, 2,3-dimethyl-2-butene, 1-decene, and vinyl chloride, and alkenyl aromatics such as styrene and divinylbenzene can be reacted with the compositions of the invention to form their respective thiocyanate derivatives.

Solvents useful as carriers for the stable compositions of the invention are those which are inert to the reaction conditions of the polymer surface treatment and resistant to organic thiocyanate formation. Solvents which are suitable include aliphatic and cycloaliphatic ethers, aliphatic and aromatic hydrocarbons, aliphatic alcohols, halogenated hydrocarbons, chlorofluorocarbons, ketones, organic acids, esters and the like inert solvents. Examples specific solvents are ethers such as 2-methoxyethanol, 1-methoxy-2-propanol, 1,4-dioxane, and tetrahydrofuran; aliphatic and aromatic hydrocarbons such as hexane, heptane, iso-octane, cyclohexane, benzene, toluene, ethylbenzene and xylene: and aliphatic alcohols such as methanol, ethanol and 2-propanol.

Halogenated hydrocarbons including methylene chloride, carbon tetrachloride, methylchloroform, 1,2-dichloroethane, their fluorine analogs and the like can be used as solvents, as well as fluorocarbon compounds such as Freon-113 (1,1,2-trichlorotrifluoroethane) and Freon 11 (trichlorofluoromethane). Substituted aromatic compounds such as dichlorobenzenes and nitrobenzene may also be used as solvents.

Ketones such as methyl ethyl ketone and methyl isobutyl ketone; organic esters such as methyl acetate, ethyl acetate, and 2-ethoxyethyl acetate; carboxylic acids such as formic acetic, propanoic acid, and butanoic acid are also useful as carriers.

These same solvents can also be used as media in which to prepare the stable thiocyanating compositions.

Solvents that react with the chlorine, or other oxidizing agent, are not as desirable as those which do not react with the oxidizing agent. Thus, if the solvent reacts with the oxidizing agent to any appreciable extent, more of the oxidizing agent is required, thus increasing the costs of production. The preferred solvents for preparing the composition are halogenated hydrocarbons, while those preferred as carriers, in addition to the halogenated hydrocarbons, will be determined by the solubility of the thiocyanogen compound and the stabilizer compound as well as the particular application in which the stable thiocyanating composition is to be employed.

The reaction for making thiocyanogen is generally conducted at ambient temperatures (20°–25° C.) and the preparation of the stable composition of thiocyanogen and an $\alpha,\beta$-unsaturated ketone is accomplished at these same temperatures. Temperatures above 50° C. for either the reaction to form thiocyanogen or the preparation of the stable thiocyanating composition are to be avoided. The molar ratio of the $\alpha,\beta$-unsaturated ketones to thiocyanogen or thiocyanogen chloride in the stable composition is at least 1/1 up to about 6/1, preferably from about 2/1 to about 4/1 and most preferred from 2/1 to about 3/1.

The following examples are representative of the preparation and use of the stable thiocyanating compositions.

EXAMPLE 1

Representative Preparation of the Stable Composition of Thiocyanogen and an $\alpha,\beta$ Unsaturated Ketone Into a flask with stirring means was placed 100 mL of reagent-grade carbon tetrachloride. Lead thiocyanate, Pb(SCN)$_2$, (7.5 g, 0.023 mole) was added while stirring the contents of the flask at room temperature (20°–25° C.). Bromine, Br$_2$ (3.2 g, 0.02 mole) was added with continued stirring until the color of the bromine disappeared. The PbBr$_2$ precipitate was removed from the solution by filtration. An $\alpha,\beta$-unsaturated ketone [1–2 moles per mole (SCN)$_2$] was then added to the thiocyanogen solution and this solution, containing the composition, was stored at ambient temperatures (optionally under a nitrogen pad) and observe periodically.

Various compounds containing similar groups and/or structures were added to a solution of a thiocyanogen prepared in the manner of Example 1. Ten mL of the thiocyanogen solution was placed in small vials and the compounds to be tested as inhibitors were added in an amount sufficient to provide a 1.0 wt. % solution. The vials were capped, stored and observed periodically. Instability was indicated by the appearance of a precipitate.

The number of days before a precipitate occurred is indicated in the following table. The test was discontinued after 150 days and the vials were not checked further.

| Compound | Days Stable |
| --- | --- |
| tetrachloro-o-benzoquinone* | >150 |
| tetrachloro-p-benzoquinone** | <2 |
| 2,5-dichloro-p-benzoquinone | <2 |
| tetramethyl-p-benzoquinone | <2 |
| tetrahydroxy-p-benzoquinone | <2 |
| hydroquinone | <2 |
| catechol | <2 |
| cumene | <2 |
| styrene | <2 |
| benzoic acid | <2 |
| maleic acid | <2 |
| mesityl oxide | <2 |
| methylvinyl ketone | >150 |

*o-chloranil
**p-chloranil

The above table illustrates that only certain $\alpha,\beta$-unsaturated ketones are effective in stabilizing thiocyanogen.

Equivalents for the o-chloranil are the unsubstituted 1,2-benzoquinone and its other halogen derivatives including those with fewer chlorines and those in which the chlorines are replaced by fluorine, bromine or iodine. The halogen derivatives of methyl vinyl ketone (MVK), wherein some hydrogens are substituted with a halogen, e.g. 4,4-dichloro-3-butene-2-one, are also equivalent with respect to their use in combination with thiocyanogen. Thiocyanogen halides, while more stable than thiocyanogen, can be stabilized over longer periods of time with the $\alpha,\beta$ unsaturated ketones of the invention.

The treatment of polymers is ordinarily accomplished by immersing the polymer article (sheet or molded item) in a solution of the stable thiocyanogen composition for a period of time sufficient to wet the surface (usually 2–10 seconds in the case of polyurethanes). Other polymers may require longer periods of immersion. The wetted polymer article is then removed and allowed to dry at ambient temperature or placed in an oven to remove the solvent and/or to complete the reaction of the thiocyanogen product with the surface of the article. Temperatures of from about ambient up to the boiling point of the solvent may be used in treating the article while those employed in evaporating the solvent from the surface may be from room temperature up to about 150° C.

The stable thiocyanating compositions produce thiocyanate moieties or functionality in the surface of the polymer. The mechanism by which the thiocyanating compositions are stabilized is not known, but they produce the thiocyanate functionality at the surface of the polymer which provides a more adherent surface as does the treatment with the unstabilized thiocyanogen.

EXAMPLE 2

Use of the Stable Thiocyanogen-o-Chloranil Composition in the Modification of a Polyurethane To a carbon tetrachloride solution of thiocyanogen prepared as in Example 1 was added 7.5 g (0.03 mole) of o-chloranil. This solution was then used to treat a specimen (½"×8"×⅛" dimensions, or 1.27 cm×20.32 cm×0.32 cm) of reaction injection molded (RIM) polyurethane by immersing it in the solution for 5 seconds at room temperature. The polyurethane specimen was then placed in an oven heated to 130°–140° C. for twenty minutes. After cooling the specimen the contact angle of 2-ethoxyethylacetate on the surface was measured. The average contact angle of 5 treated samples was 6°±1°, while for 5 untreated samples the contact angle was 26°±2°. The contact angle for treatment with freshly prepared thiocyanogen was 7°±2°. The more wettable surfaces give a smaller contact angle.

The procedure employed for measuring contact angle follows:

Procedure

1. Place polymer specimen to be evaluated in a Kayeness, Inc. Contact Angle Viewer, Model D-1060.
2. Place a drop of an appropriate liquid on the specimen from a height of one inch.
3. Rotate the protractor so that the 90/90 vertical line is tangent to the arc at the leading edge of the drop. Read the contact angle at the arrow point.
4. Repeat step 3 at the other edge of the drop.
5. Average the two readings.
6. Repeat steps 2, 3, 4 and 5 four times and average the four values to obtain the experimental contact angle.

EXAMPLE 3

Isolation of the Stable Composition of Thiocyanogen and o-Chloranil

Into a flask containing a magnetic stirring bar was placed 200 mL of a stabilized methylchloroform. To this was added 10.0 grams of potassium thiocyanate (KSCN) with stirring. Next 200 milliliters of stabilized methylchloroform containing 1.4 g of chlorine, $Cl_2$, was added to the stirred mixture. Stirring was continued for one hour or until the odor of chlorine was no longer detected in the vapor space of the flask. Precipitated KCl solids were separated from the reaction mixture by filtration. Then, 9.9 g of o-chloranil was added to the filtered thiocyanogen solution while agitating. The solution was allowed to stand for 48 hours.

The above prepared solution was poured into a large boiling flask and distilled under vacuum at about 40° C. to isolate the composition of thiocyanogen and o-chloranil. A portion (0.3046 g) of the solid dark red composition was dissolved in 25 mL of methanol. This solution was used to treat a piece of RIM polyurethane as described in Example 2. The contact angle of 2-methoxyethanol on the treated RIM was measured. A value of 17 for the treated RIM was found as compared to 44 for untreated and 43 for RIM treated with methanol only.

Infrared spectroscopy of thiocyanogen solutions in $CCl_4$ normally show a sharp characteristic peak at 2160 $cm^{-1}$ which on standing decreases rapidly over a period of 24 hours, presumably due to the formation of the inert thiocyanogen polymer.

A solution of thiocyanogen and o-chloranil in $CCl_4$ as prepared in Example 1 was examined by infrared spectrocopy. While the peak characteristic of thiocyanogen was apparent, another larger peak was observed at 2000 $cm^{-1}$. After 24 hours, reexamination of the $CCl_4$ solution of the product showed that the peak at 2000 $cm^{-1}$ had greatly increased, while that at 2160 $cm^{-1}$ had decreased. The absorbance at 2000 $cm^{-1}$ is characteristic of an organic isothiocyanate (R—N=C=S). Organic thiocyanates on the other hand (R—S—C≡N) exhibit weak, but sharp absorption at 2160 $cm^{-1}$.

Another analysis of the $CCl_4$ solution of thiocyanogen and o-chloranil was made using liquid chromatography/mass spectroscopy. The following three main clusters were observed:

1. $C_6Cl_3O_2(SCN)_2$, indicating the addition of the thiocyanogen, $(SCN)_2$, across the double bond followed by loss of chlorine.
2. $C_6H_2Cl_3O_2(SCN)$, indicating the addition of HSCN across the double bond followed by loss of chlorine.
3. $C_6H_2Cl_4O_2$, indicating the addition of hydrogen across the double bond.

Another sample of the same solution was evaporated to dryness in a probe cup of a mass spectrometer. While next to the source the dried sample was heated at the rate of 30° C./minute. Again three main clusters were observed as follows:

1. $C_6Cl_3O_2(SCN)$
2. $C_5Cl_2O(SCN)$
3. $C_6Cl_2O_2(SCN)$

The above as well as the previous mass spectroscopic data indicates attachment of the (SCN) to the o-chloranil, but mass spec cannot determine whether the bond is a thiocyanate or an isothiocyanate, i.e. whether the carbon is attached to the nitrogen or to the the sulfur, respectively.

EXAMPLE 4

Preparation of the Composition Containing Thiocyanogen Chloride (SCNCl) and o-Chloranil To 100 mL of $CCl_4$ containing 13 g of $Pb(SCN)_2$ was added 5.4 g of bromine with stirring, which was continued until the reaction mixture no longer shows the bromine color. The solution was filtered to remove $PbBr_2$ and a clear yellow solution of $(SCN)_2$ was obtained. Then 100 mL of $CCl_4$ containing 2.4 g chlorine was added with stirring to the $(SCN)_2$ solution. The color of the solution changed to a deeper gold color which is typical of thiocyanogen chloride (SCNCl). A quantity (25 mL) of this solution was added to 75 mL of $CCl_4$ which contained o-chloranil (2.5 g). Another 25 mL of the solution of SCNCl was added to 75 mL of $CCl_4$ without o-chloranil. Both solutions were bottled and sealed and observed periodically. Thiocyanogen chloride is more stable than thiocyanogen, but after 64 days a precipitate had formed in the bottle without o-chloranil. After 76 days the bottle containing the combination of SCNCl and o-chloranil showed no precipitate and remained clear. The molar ratio of o-chloranil to SCNCl in the example was 1.2/1.

EXAMPLE 5

Preparation of the Composition Containing Thiocyanogen and Methyl Vinyl Ketone

To a quantity of thiocyanogen (0.005 mole) in 100 mL stabilized methylchloroform was added 0.83 mL (0.01 mole) of methyl vinyl ketone. The solution at room temperature was stirred, bottled and sealed. The sample was observed periodically and there was no precipitate and sample was clear after ~510 days (17 months) storage at ambient temperature. The molar ratio of methyl vinyl ketone to thiocyanogen was 2/1.

In another experiment conducted in the manner of Example 1, o-chloranil was combined with $(SCN)_2$ at a 5/1 molar ratio in $CCl_4$ solution. The solution was bottled, sealed and observed at intervals over a period of time. Only a very slight amount of precipitate was observed after 17 months of storage at ambient conditions.

The experiments in Example 5 above show that both o-chloranil and methyl vinyl ketone stabilize thicyanogen solutions for extended periods of time. The previous Example 4 shows that the stability of thiocyanogen chloride is extended by the addition of o-chloranil.

To show that the stable composition reacts with organic compounds to form organic thiocyanates the following experiment was conducted.

EXAMPLE 6

Reaction of the Stable Thiocyanating Composition with an Organic Cycloaliphatic Compound To 15 mL of reagent grade cyclohexene in a clear glass container was added 25 mL of a solution of the combination of o-chloranil and thiocyanogen, prepared as in Example 1.

The mixture was exposed to UV-light for 20 minutes while stirring. The resulting composition, as determined by gas chromatography/mass spectrometry, contained: dithiocyanato cyclohexanes, thiocyanato or isothiocyanato cyclohexenes, chlorothiocyanato cyclohexane, chlorocyclohexenes.

It should be noted that when halogen-containing α,β-unsaturated ketones are used to stabilize thiocyanogen, halothiocyanato products are also obtained. If one does not want a halogen-containing product, a non-halogen-containing α,β-unsaturated ketone should be used. Likewise, the use of a thiocyanogen halide will produce a halogen-containing product.

While attempts have been made to characterize a reaction product which may be produced when the thiocyanating compound and an α,β-unsaturated ketone are placed together in an inert organic solvent, results have been inconsistent. The structure of the compound produced, if any, is not the same with an aliphatic compound, e.g. methyl vinyl ketone, as that of the aromatic compounds, e.g. tetrachloro-o-benzoquinone. The same stabilizing and thiocyanating components placed in different solvents also give inconsistent structures.

What is claimed is:

1. A stable thiocyanating composition comprising in combination (a) thiocyanogen or a thiocyanogen halide with (b) an α,β-unsaturated ketone in (c) an inert organic solvent.

2. The composition of claim 1 wherein the (b) component is a 1,2-benzoquinone, a halo-substituted 1,2-benzoquinone, methyl vinyl ketone or a halo-substituted methyl vinyl ketone.

3. The composition of claim 2 wherein the (a) component is thiocyanogen.

4. The composition of claim 2 wherein the (a) component is a thiocyanogen halide.

5. The composition of claim 3 wherein the inert solvent is an aliphatic hydrocarbon.

6. The composition of claim 3 wherein the inert solvent is a halogenated hydrocarbon.

7. The composition of claim 6 wherein the halogenated hydrocarbon is an aliphatic halogenated hydrocarbon.

8. The composition of claim 7 wherein the halogenated aliphatic hydrocarbon is an aliphatic chlorocarbon.

9. The composition of claim 8 wherein the aliphatic chlorocarbon is carbon tetrachloride.

10. The composition of claim 8 wherein the aliphatic chlorocarbon is methylchloroform.

11. The composition of claim 7 wherein the halogenated aliphatic hydrocarbon is an aliphatic chlorofluorocarbon.

12. The composition of claim 11 wherein the chlorofluorocarbon is trichlorofluoromethane or trichlorotrifluoroethane.

13. The composition of claim 3 wherein the inert solvent is an organic ether, ketone, alcohol, carboxylic acid or ester.

14. The composition of claim 4 wherein the inert solvent is an aliphatic hydrocarbon.

15. The composition of claim 4 wherein the inert solvent is a halogenated hydrocarbon.

16. The composition of claim 15 wherein the halogenated hydrocarbon is an aliphatic halogenated hydrocarbon.

17. The composition of claim 16 wherein the halogenated aliphatic hydrocarbon is an aliphatic chlorocarbon.

18. The composition of claim 17 wherein the aliphatic chlorocarbon is carbon tetrachloride.

19. The composition of claim 17 wherein the aliphatic chlorocarbon is methylchloroform.

20. The composition of claim 16 wherein the halogenated aliphatic hydrocarbon is an aliphatic chlorofluorocarbon.

21. The composition of claim 20 wherein the chlorofluorocarbon is trichlorofluoromethane or trichlorotrifluoroethane.

22. The composition of claim 4 wherein the inert solvent is an organic ether, ketone, alcohol, carboxylic acid or ester.

23. A method of stabilizing thiocyanogen or thiocyanogen chloride which comprises adding an α,β-unsaturated ketone to thiocyanogen or a thiocyanogen halide in an inert solvent.

24. The method of claim 23, wherein the α,β-unsaturated ketone is 1,2-benzoquinone, methyl vinyl ketone or halo-derivatives of 1,2-benzoquinone or methyl vinyl ketone.

25. The method of claim 24, wherein the inert solvent is a halogenated aliphatic hydrocarbon.

26. The method of claim 25, wherein the halogenated aliphatic hydrocarbon is carbon tetrachloride.

27. The method of claim 25, wherein the halogenated aliphatic hydrocarbon is methylchloroform.

28. A method of thiocyanating the surface of a polymer which contains unsaturation comprising contacting said surface with a solution of a stable composition of claim 1.

29. The method of claim 28 wherein the polymer is a polyurethane.

30. The method of claim 29 wherein the stable composition is that of tetrachloro-1,2-benzoquinone and thiocyanogen in a halogenated aliphatic hydrocarbon.

* * * * *